(12) United States Patent
Sparey-Taylor et al.

(10) Patent No.: US 7,731,412 B2
(45) Date of Patent: Jun. 8, 2010

(54) FLUID-HANDLING APPARATUS AND METHODS

(75) Inventors: Graham Sparey-Taylor, St. Athan St. (GB); David Strand, Sherborn, MA (US); David Barrow, Cardiff (GB)

(73) Assignee: Protasis Corporation, Marlborough, MA (US)

( * ) Notice: Subject to any disclaimer, the term of this patent is extended or adjusted under 35 U.S.C. 154(b) by 0 days.

(21) Appl. No.: 11/506,771

(22) Filed: Aug. 10, 2006

(65) Prior Publication Data

US 2007/0140041 A1    Jun. 21, 2007

(51) Int. Cl.
*B01F 11/02*    (2006.01)
*B01F 7/00*    (2006.01)

(52) U.S. Cl. .................... 366/127; 366/143; 366/151.1; 366/182.4; 366/DIG. 4

(58) Field of Classification Search ............ 366/DIG. 4, 366/127, 143, 151.1, 182.4
See application file for complete search history.

(56) References Cited

U.S. PATENT DOCUMENTS

| 6,210,128 | B1 | 4/2001 | Rife et al. | |
| 6,244,738 | B1 | 6/2001 | Yasuda et al. | 366/114 |
| 6,777,245 | B2* | 8/2004 | Wixforth | 436/180 |
| 2002/0083771 | A1* | 7/2002 | Khuri-Yakub et al. | 73/589 |
| 2007/0140041 | A1* | 6/2007 | Sparey-Taylor et al. | 366/127 |

FOREIGN PATENT DOCUMENTS

| JP | 2001276593 | 9/2001 |
| WO | WO 02/28532 A2 | 4/2002 |

\* cited by examiner

*Primary Examiner*—Tony G Soohoo
(74) *Attorney, Agent, or Firm*—Banner & Witcoff, Ltd.

(57) ABSTRACT

Fluid processing apparatus comprises a fluid-handling manifold comprising a manifold body having at least a first fluid duct and a second fluid duct. The first and second fluid ducts are in fluid communication with each other at a microfluidic junction of the fluid-handling manifold. The manifold body further comprises a transducer operative to generate ultrasonic acoustic traveling wave radiation into fluid in the microfluidic junction from an active surface toward a non-reflective boundary of the microfluidic junction. The microfluidic junction is operative to pass fluid received from the first and second duct, with micro-mixing effected by the traveling wave radiated into the junction during the fluid flow.

10 Claims, 5 Drawing Sheets

FLUID-HANDLING APPARATUS AND METHODS

Priority Applications

This application claims the priority benefit of U.S. Utility patent application Ser. No. 10/616,372, filed on Jul. 9, 2003 and entitled "Fluid-Handling Apparatus and Methods" and U.S. Provisional Application No. 60/415,719, filed on Oct. 3, 2002 and entitled "Fluid-Handling Apparatus and Methods," the entire disclosure of which is hereby incorporated herein by reference in its entirety for all purposes.

CROSS-REFERENCED APPLICATIONS

This application is related to commonly assigned co-pending PCT Application No. PCT/US03/17274 filed on Jun. 3, 2003 and entitled "Device and Method for Ultrasonically Manipulating Fluid-Born Particles," the entire disclosure of which is hereby incorporated herein by reference in its entirety for all purposes.

INTRODUCTION

The present invention relates to certain novel devices and methods for processing fluids, employing ultrasonic acoustic radiation traveling waves. In particular, the invention is directed to devices and methods employing an ultrasonic transducer operable for actuation to generate ultrasonic acoustic traveling waves to effect fluid mixing in a fluid-handling manifold.

BACKGROUND

Ultrasonic waves are produced in two generic forms, transverse and longitudinal. Transverse waves travel across the active surface of the source media and are termed as surface acoustic waves. Longitudinal waves have a wave front that travels normal to the source media. Longitudinal waves fall into two categories, standing waves, and traveling waves. Where an electric periodic wave function signal is applied to a resonant piezoelectric transducer, for example, a reactive mechanical force is derived. If a reflective boundary, i.e., a boundary in the line of travel of the traveling wave that reflects back at least a majority of the wave energy, is placed as to conform to Snell's law, substantial or total internal reflection will be obtained and a steady state standing wave environment is established. In the absence of a reflective boundary, i.e., if the acoustic radiation is propagated to a boundary that passes or absorbs more than half of the incident wave energy, a traveling wave is established, optionally a steady state traveling wave depending on the function of the operating signal generated by the transducer's actuation circuitry.

Fluid-handling devices are known, having a portable, disposable or interchangeable fluid-handling manifold having one or more inlet ports and perhaps one or more outlet ports, providing fluid communication with a fluid duct in the manifold. Such fluid-handling devices may be self-contained or intended for use as a component of a larger system. Known devices of this type having capillary or microfluidic ducts have drawbacks, such as, for example, significant flow resistance and difficulty mixing in the laminar flow regime. Flow is laminar for microfluidics where the Reynolds numbers are less than about 2000, and the lack of turbulence makes mixing difficult. In microfluidic laminar flow, for example, two fluids of different composition can pass side-by-side with little or no intermixing except by diffusion. Rife et al. in U.S. Pat. No. 6,210,128 suggest miniature fluid pumps and mixers having capillary flow lines feeding fluid into large size fluid processing reservoirs. Acoustic radiation is generated to circulate fluid in the reservoirs.

It is an object of the present invention to provide improved fluid-handling apparatus and methods for processing fluid, employing ultrasonic acoustic radiation including at least traveling wave ultrasonic acoustic radiation.

SUMMARY

In accordance with a first aspect, fluid processing apparatus disclosed here comprises a fluid-handling manifold and, optionally, other components and devices that may be fluidically, electrically, electronically and/or otherwise connected to the fluid-handling manifold, e.g., one or more fluidic components integral with the fluid-handling manifold and operative on fluid in the manifold body. The fluid-handling manifold is operative to process fluid passed through the manifold body, for example, to process all or a portion or selected component(s) of such fluid. As used here fluid refers to gases, liquids, supercritical fluids and the like, optionally containing dissolved species, solvated species and/or particulate matter. Fluids also refer to multiple fluids of different types present together. The fluid-handling manifold comprises a manifold body that has at least a first fluid duct and a second fluid duct in fluid communication with each other in the manifold body at a microfluidic junction operative to pass fluid received from the first and second ducts. The microfluidic junctions, and in certain preferred embodiments the inlet and outlet ducts also, are microfluidic or microscale. As used herein, the term "microscale" refers to flow channels and other structural elements of the fluid-handling device having cross-sectional dimension (diameter, width or height) between 500 microns and 100 nanometers such that, at the small end of that range, a microfluidic junction or duct would have, for example, cross-sectional area of about 0.01 square microns. Typically the cross-sectional area of a microfluidic junction is less than about 0.25 square millimeter, preferably, about 0.05 to 0.15 square millimeter, e.g. about 0.08 square millimeter. Microscale and "microfluidic" mean the device operates effectively on micro-scale fluid samples, typically having fluid flow rates as low as about 1 ml/minute, preferably 100 ul per minute or less, more preferably 10 ul per minute or less, most preferably 1 ul per minute, or less, for example 100 nanoliters/minute total fluid volume for a microfluidic junction in accordance with certain preferred embodiments is about 0.1 microliter to 5.0 microliter, preferably about 100 nanoliters to 1.0 microliter. Total fluid volume for a manifold body according to certain preferred embodiments is about 10 ml or less, preferably 1 ml or less, e.g. 100 microliters or even 1 microliter or less, for example, about 100 nanoliters.

In certain preferred embodiments the manifold body, optionally with other components of the fluid-handling manifold, is in the form of (e.g., is "packaged as") a portable, disposable or interchangeable cartridge or the like. The fluid-handling manifold further comprises a transducer operative to generate ultrasonic acoustic traveling wave radiation into the microfluidic junction toward a non-reflective boundary not more than 300 microns from the active transducer surface. The non-reflective boundary is substantially non-reflective of the ultrasonic traveling wave radiation and may be, for example, the opposite wall or other surface of the microfluidic junction, optionally being a wall or other surface of glass, plastic, metal, ceramics or silica material used to form some or all of the manifold body. The transducer may be coupled to the manifold body in any number of ways. In certain preferred embodiments the transducer is coupled to the outside of the manifold body with an adhesive such as an epoxy or the like. In other embodiments the active surface of the transducer forms all or part of the fluid-contacting surface of the microfluidic junction. In certain preferred embodiments, fluid to be mixed is flowing into and through the microfluidic junction and the transducer is operative to generate ultrasonic acoustic traveling wave radiation into the microfluidic junction substantially orthogonal to the local fluid flow through the microfluidic junction, that is, substantially orthogonal to the axial or overall direction of flow of fluid through the microfluidic junction. In other embodiments the transducer may be positioned or mounted so as to produce acoustic radiation in acute or obtuse angles to the local fluid flow.

Fluid-handling manifolds of fluid processing apparatus disclosed here are operative to process fluid stored in or flowed through the microfluidic junction of the manifold body by ultrasonic mixing and, optionally, also by other means such as, for example, additional ultrasonic and/or non-ultrasonic processing, for example, testing, sensing, flow measurement or control, or otherwise analyzing the fluid or some portion or component(s) of the fluid. In certain embodiments, the fluid-handling manifold may be operative to temporarily or permanently store fluid in a duct or other fluid zone of the manifold body. Certain preferred embodiments of the fluid-handling manifold are operative to pass fluid to other devices or apparatus, etc.

The fluid-handling devices disclosed here offer advantages in systems for chemical analysis, testing, synthesis or other processing of fluids. Depending on the particular design and intended use of the fluid-handling device, such advantages may include, for example, increased or otherwise controlled rates of reaction, heating, cooling or other actions on the fluid, lower overall processing times, reduced power consumption, reduced quantities of regents, and improved portability. The fluid-handling devices disclosed here may provide stand-alone functionality, not requiring other system components to perform one or more intended operations on a fluid sample passed into or through the manifold, or may have plug-in functionality, being useable as a component of a larger system, e.g., by being inserted into an access port or the like to perform one or more desired functions on a sample of fluid received from the larger system.

The manifold body of the fluid-handling manifold preferably is formed as a unitary body, such as, for example, a block of glass, plastic or other material, or as an integral body, such as, for example a laminated body having multiple layers of glass, plastic and/or other materials joined bonded, clamped or otherwise joined in surface to surface contact. In certain embodiments, the manifold body comprises both a monolithic body and a laminated body joined together, optionally with fluidic and/or other communication between them. The manifold body typically is able to tolerate fluid pressures (meaning fluid pressures in the microfluidic junction and preferably at all locations along the first and second ducts as well) of at least 25 psi.) The manifold body is operative to receive fluid via one or more inlet ports at the surface of the manifold body, each inlet optionally being fitted with a suitable connection socket, nipple, controllable valve or the like. The manifold body, in addition to having one or more inlet ports, optionally has one or more outlet ports and/or fluid storage reservoirs or zones, in some instances referred to as fluid cells, in fluid communication with fluid ducts in the manifold body. Fluid is passed by the first and/or second duct to the microfluidic junction. A duct may be referred to in some instances in this disclosure and in the claims below as a fluid duct or channel or fluid zone or the like. The ducts of the manifold body may be formed in or on the manifold body.

Ducts may be formed, for example, within a laminate layer and/or at an interface of laminate layers of the manifold body. Ducts also may be formed as a "via" passing through the plane of one or more laminate layers, e.g., to provide fluid communication from one plane to another within the manifold body. Also, ducts may be formed within a unitary body of glass or plastic. Suitable manufacturing techniques and materials for the manifold bodies of the fluid-handling manifolds disclosed here, and suitable fluidic connection means and suitable auxiliary components to be carried on-board the manifold body or otherwise integrated with the fluid-handling manifold, will be apparent to those skilled in the art given the benefit of this disclosure. Exemplary techniques and materials for such manifold bodies and fluid connections and on-board components are taught in WO 0228532 A2 entitled Microfluidic Substrate Assembly And Method For Making Same, the entire disclosure of which is incorporated herein by reference for all purposes.

The microfluidic junction is operative to pass a flow of fluid comprising fluid received from the first duct and fluid received from the second duct. For convenience, fluid in the microfluidic junction at any given point in time may be referred to in some instances here and in the claims below as a "local fluid flow." The microfluidic junction may have well defined boundaries or be only generally distinguished from the two or more ducts that feed fluid to it, except that it will include at least a zone or portion into which the transducer of the fluid-handling manifold is operative to generate ultrasonic acoustic traveling wave radiation, as discussed further below. Thus, for example, ducts may intersect at one end of the microfluidic junction at an acute or oblique angle to each other or at 90 degrees to each other. The microfluidic junction in certain embodiments is at a T-connection of two ducts, with any of the three legs of the "T" being the downstream leg into which the other ducts feed fluid. Thus, for example, the downstream duct may be a straight line extension of one of the intersecting ducts. Alternatively, the microfluidic junction in certain embodiments is at a Y-connection of two ducts, with any of the three legs of the "Y" being the downstream leg into which the other two feed fluid, but preferably the bottom of the "Y" (i.e., the leg having the same angle of intersection with the other two legs) being the downstream duct into which the others feed fluid. It should be understood in this regard, that the microfluidic junction is said to be "at" the connection of two or more ducts in the sense that in different embodiments it may include the zone where feed ducts form a faired connection with each other. Alternatively, or in addition, it may include a portion of a duct or fluid cell or zone downstream from such point at which the feed ducts meet. The microfluidic junction may optionally be uniform in cross-sectional size and shape or may vary. It may be larger, smaller or the same in cross-sectional area as the combined cross-sectional areas of the ducts that feed into it. In accordance with certain preferred embodiments, the microfluidic junction is part or all of an elongate fluid channel having a constant cross-section that is circular, semi-circular, square, rectangular or triangular. It will be within the ability of those skilled in the art, given the benefit of this disclosure, to design manifold bodies having microfluidic junctions suitable to any of innumerable intended uses and conditions.

To generate the ultrasonic acoustic traveling wave radiation into the microfluidic junction, the fluid-handling manifold comprises a transducer, as disclosed above. As used here and in the claims below, the term "comprises" a component or feature (or "comprising" or other syntactic or grammatical variations) means one or more such components or features, that is, at least one of such components or features. Thus, the phrase "comprises a transducer," means at least one transducer. Preferably, the transducer is mounted on the surface of the manifold body or mounted or embedded within the manifold body or otherwise integrated with the manifold body. At least one such transducer is operative to generate ultrasonic acoustic traveling wave radiation into the microfluidic junction of the manifold body, preferably at frequencies of 6-200 MHz. The fluid-handling manifolds disclosed here optionally may have multiple manifold bodies, and one or more of such manifold bodies may, optionally, have multiple microfluidic junctions, each optionally having one or more associated transducers operative to generate ultrasonic acoustic traveling wave radiation. In certain preferred embodiments, the fluid processing apparatus comprises piezoelectric material overlying a surface of the manifold body. Also, the fluid processing apparatus may optionally comprise a magnetostrictive transducer, an electrostatic transducer, a thermoacoustic transducer, or the like.

Typically, such transducer is located at the surface of the microfluidic junction in an area where fluid mixing is to be performed. In certain preferred embodiments, the active material of the transducer, e.g., sheet-like or plate-like piezoelectric material, is integrated into the manifold so as to form at least part of the surface of the microfluidic junction that directly contacts fluid. Alternatively, the active material of the transducer may overlay a surface or wall of the manifold body so as to pass ultrasonic acoustic traveling wave radiation through such surface or wall into fluid passing through the microfluidic junction. As used here, the "active surface" of the transducer is the surface of the microfluidic junction that contacts fluid in the microfluidic junction and at which ultrasonic acoustic traveling wave radiation is passed into the fluid. Such active surface may be the surface of material that is itself responsive to a wave-generating signal, e.g., piezoelectric material, or may be the surface of an inactive or non-responsive material, e.g., glass or plastic, through which an adjacent (e.g., overlying or laminated) transducer material passes ultrasonic acoustic traveling wave radiation. Thus, the non-reflective boundary of the microfluidic junction, being not more than 300 microns from the active surface, may nevertheless be more than 300 microns from the surface of signal-responsive material of the transducer overlying a non-responsive laminate layer or wall of the manifold body. The non-reflective boundary of the microfluidic junction may optionally be a surface of another laminate layer or other surface of the manifold body. Alternatively, such non-reflective boundary of the microfluidic junction may be an air-liquid interface.

In certain preferred embodiments, mixing of a fluid by ultrasonic acoustic traveling wave radiation by the fluid handing manifold combines multiple fluid flow streams, optionally with other fluid processing also occurring in the manifold. In certain preferred embodiments, mixing of a fluid by ultrasonic acoustic traveling wave radiation by the fluid handing manifold homogenizes or further homogenizes a fluid in or flowing through the manifold, optionally with other fluid processing also occurring in the manifold. In certain preferred embodiments, mixing of a fluid by ultrasonic acoustic traveling wave radiation by the fluid handing manifold maintains particles in suspension in a fluid stored in or flowing through the manifold, optionally with other fluid processing also occurring in the manifold. There is significant use for the fluid-handling devices disclosed here as part of a larger system. Examples of such systems include but are not limited to HPLC, NMR, CE, GC, isoelectric focusing, LC, FPLC, GCMS, electrophoresis, SCF chromatography, column chromatography, and hyphenated method systems. Other systems suitable to include the fluid-handling devices disclosed here will be apparent to those skilled in the art given the benefit of this disclosure. Certain such just mentioned embodiments may be used, for example, in the packing of solid phase extraction (SPE) particles into a column, e.g., for liquid chromatography, especially high-pressure liquid chromatography ("HPLC"). In certain especially preferred embodiments providing excellent functionality and compactness, the HPLC column is within the manifold, and the manifold is then operative to process samples of the same or different fluid through the packed column at HPLC pressures, of at least, e.g., 1000 psi (that is, the manifold body can withstand and operate at fluid pressure of at least 1000 psi and may in some cases, of course, tolerate even higher pressures), preferably at least 6000 psi and in some preferred embodiments at least 10,000 psi. Certain preferred embodiments, for example embodiments that are operative to perform liquid chromatography, especially those operative to perform high pressure liquid chromatography, employ a laminated manifold body wherein at least one and preferably multiple laminations of the laminated body are formed of plastic preferably, polyether ether ketone ("PEEK"). In accordance with other embodiments, employing a manifold body that is formed as a unitary body, preferably the manifold body is formed of a monolithic block of glass, plastic, preferable PEEK, or other suitable material through which the ducts extend. PEEK has superior chemical resistance and high-pressure tolerance allowing for its use in harsh chemical environments, and retains its flexural and tensile properties at elevated temperatures. Glass and carbon fibers may be added to PEEK or other plastics to enhance mechanical and thermal properties. In other preferred embodiments the manifold body is formed of laminated layers of polycarbonate. In other embodiments the manifold body is formed of metal. Examples of suitable metals include but are not limited to stainless steel, aluminum, various alloys, etc. In still other embodiments the manifold body is formed of materials such as glass, silica, ceramic or any suitable combination or composite of these materials. Additives such as dyes or particulates may be added to such materials to obtain desired characteristics.

In certain preferred embodiments, mixing of a fluid by ultrasonic acoustic traveling wave radiation by the fluid handing manifold accelerates or otherwise controls a reaction in fluid stored in or flowing through the manifold, optionally with other fluid processing also occurring in the manifold. Other fluid processing involving mixing of a fluid by ultrasonic acoustic traveling wave radiation by embodiments of the fluid handing manifolds disclosed here will be apparent to those skilled in the art given the benefit of this disclosure. Also, as indicated above, certain preferred embodiments of the fluid processing manifolds disclosed here are operative to process fluid not only by mixing by ultrasonic acoustic traveling wave radiation, but also, for example, by testing, sensing or otherwise analyzing the fluid or some portion or component(s) of the fluid, by mechanical mixing, by flow rate or pressure control, or by other operations.

The fluid-handling manifold optionally comprises one or more additional components, for example, one or more additional components integral with the manifold body. In certain embodiments, the additional component, referred to in some instances here and in the claims below as a "component-on-board," is in fluid communication with a duct, optionally being in fluid communication with fluid in the microfluidic junction and optionally being operative on the fluid. The integral fluidic component may, for example, be mounted to the surface of the manifold or embedded within the manifold or, in the case of a fluid-handling device in the form of a cartridge, the integral fluidic component may be housed within or otherwise mounted to a housing of the cartridge. As used here and in the claims below, the phrase "operative on fluid in the manifold" means that the fluidic component is operative to interact with some or all of the fluid in the manifold, or with a component of the fluid. It may be operative, for example, to heat or cool the fluid or to manipulate, sense, test, evaluate or control fluid in the manifold body. In certain preferred embodiments, the integral fluidic component is an observation window or a sensor exposed to fluid in the manifold, e.g., a pH sensor, pressure sensor, temperature sensor, conductivity sensor, etc.

In accordance with certain embodiments, the aforesaid additional component of the fluid-handling manifold is a second transducer. Optionally, such second transducer is operative to generate ultrasonic acoustic standing wave radiation into fluid in a duct or other fluid containing cell or zone of the manifold body, preferably into the microfluidic junction, toward a reflective boundary of the manifold body to establish a standing wave in the fluid. Optionally, the second transducer is operative to generate ultrasonic acoustic traveling wave radiation into the microfluidic junction toward a non-reflective boundary. In accordance with certain such embodiments, the first and second transducer are radially aligned and axially spaced from each other in the direction of flow through the microfluidic junction, and each is operative to generate ultrasonic acoustic traveling wave radiation into the microfluidic junction substantially orthogonal to local fluid flow through the microfluidic junction from an active surface to a non-reflective boundary of the manifold not more than 300 microns from the active surface.

In accordance with certain embodiments, the aforesaid additional component of the fluid-handling manifold is a mechanical mixer operative to mix fluid in the manifold body. In accordance with certain embodiments, the aforesaid additional component of the fluid-handling manifold is a sensor operative to detect a condition of fluid in the manifold. Optionally the sensor is operative to measure or otherwise detect the temperature, pressure, fluid flow rate or an optical property of the fluid. In accordance with certain embodiments, the aforesaid additional component of the fluid-handling manifold is a valve operative to control a flow of fluid in the manifold body, e.g., operative to control flow into or out of the manifold body. In accordance with certain such embodiments, the transducer is operative to generate ultrasonic acoustic traveling wave radiation into the valve.

In accordance with a method aspect, a method of mixing fluid comprises providing a fluid-handling device as disclosed above; introducing fluid into the manifold body, including at least into the microfluidic junction, preferably as a flow of fluid from both a first and second duct; and energizing the transducer to generate ultrasonic acoustic traveling wave radiation into the microfluidic junction, preferably orthogonal to local fluid flow through the microfluidic junction. In accordance with certain preferred embodiments, the transducer is energized at 6-200 MHz and at 10-30 volts, preferably at about 20 volts for mixing an otherwise substantially laminar fluid, especially an aqueous fluid, across a 300 um wide microfluidic junction (i.e., across a distance of 300 microns from the active surface of the transducer to the non-reflective opposite surface of the microfluidic junction). In accordance with other preferred embodiments, it is even more preferable to energize the transducer at 30-200 MHz. In accordance with certain preferred embodiments, the transducer is also actuated or energized to generate an ultrasonic acoustic standing wave in fluid in the manifold body. Such standing wave actuation of the transducer may be performed sequentially with the traveling wave actuation, or alternatingly, or otherwise. In embodiments having multiple transducers, they may be actuated sequentially or simultaneously, depending largely on the desired mixing and other effect(s) to be achieved. It will be within the ability of those skilled in the art to employ actuation energies and timing suitable for a particular fluid-handling device and fluid processing requirement.

BRIEF DESCRIPTION OF THE DRAWINGS

Certain preferred embodiments are described below with reference to the accompanying drawings in which.

It should be understood that the appended figures are not necessarily to scale. Directional references in the discussion below, such as up, down, right, left, etc., unless otherwise stated, refer to the orientation shown in the particular drawing in question. In that regard, it should be understood that the fluid-handling manifolds disclosed here may or may not require a particular orientation relative to gravity, depending upon the design of the particular device and the environment in which it is to be used.

DETAILED DESCRIPTION OF CERTAIN PREFERRED EMBODIMENTS

From the above disclosure and the following detailed description of various preferred embodiments, it will be recognized by those skilled in the art, that the novel devices and methods disclosed here have advantageous functionality applicable to fluid mixing in numerous different environments. As noted above, ultrasonic waves are produced in two generic forms, transverse and longitudinal. Longitudinal waves fall into two categories, standing waves and traveling waves. When an electric periodic wave function signal is applied the active material of a resonant piezoelectric transducer or other suitable transducer, a mechanical reaction results in the active material. If a reflection boundary is placed opposite the active surface of the transducer as to conform to Snell's law, total internal reflection can be obtained and a steady state standing wave environment established. If the opposite boundary is a non-reflective boundary, a steady state traveling wave can be established. In that case, if a fluid (liquid or gaseous) is in direct contact with the active surface, actuation of the transducer generates a traveling wave in the fluid and the traveling wave has a persuasive force on the fluid, changing or modifying or otherwise interfering with the fluid's original travel path in the microfluidic junction. This phenomenon has been characterized as quartz wind by Nyborg. The fluid processing devices disclosed here achieve fluid mixing in the path of ultrasonic traveling wave radiation generated into a micro-scale mixing zone, such as the junction of two or more capillaries or the like. Without wishing to be bound by theory, the resultant mixing effect in the fluid is found to be dependent, generally, on the multiplied vectors of the transducer pressure and fluidic pressure. This action and reflection provides the basis for micro-mixing in accordance with this disclosure, including mixing of a single fluid in the microfluidic junction, or mixing of multiple fluids or fluids comprising suspended particles. Further, due to interactions within the fluid, provided the body of fluid is accelerated to shear the fluid, forces currently understood to be Reynolds shear stresses can in certain especially preferred embodiments give rise to vortex type actions resulting in highly thorough and efficient fluid mixing.

The fluid introduced into the fluid zone may be any number of fluids, alone, in sequence, or in combination. The fluid may be a suspension or otherwise contain particulate matter. In certain embodiments two or more simultaneously flowing fluids are mixed by application of acoustic radiation in the microfluidic junction. In applications where the fluids are under high pressure, laminar flow may prevent adequate mixing. The application of acoustic radiation, specifically traveling waves, in accordance with the methods and apparatus disclosed here forces the laminar flows into each other, thereby accelerating mixing. Effects caused by the acoustic radiation impinging on a boundary cause further mixing. Suspensions and particulate matter may also be mixed using this process, preventing settling of the suspension or particulate matter.

Typically the transducer is energized at a high frequency, e.g., 6 MHz-200 MHz, with sin, cos, square or sigmoid delta function. The transducer's mechanical damping effect typically will round any emitted traveling wave and, therefore, it is generally preferable to use a signal wave for high impact and mixing efficacy. Generated acoustic pressure gradients cause fluid layers closest to the transducer to move in the direction of the gradient path, until a flow boundary is reached, e.g., the opposite wall of the microfluidic junction, causing the fluid, in certain preferred embodiments, to deflect or turn and swirl, resulting in mixing with adjacent fluid. In accordance with preferred embodiments, a transducer is operative to generate a traveling wave in the microfluidic junction effective as a mixing wave at a power and frequency that does not fully attenuate within the fluid before the opposite fluid boundary, to substantially fully mix fluid(s) within the attenuation zone of the traveling wave. The term "mixing wave" as used here refers to the motive force exerted on the fluid by the traveling wave that moves the fluid in a direction away from the transducer toward or to the fluid boundary substantially opposite the transducer. The boundary may be the opposite side of the microfluidic junction, or an interface of the fluid with another fluid, e.g., a transition from fluid to air. A certain percentage of the traveling wave energy in certain embodiments is reflected back at the boundary. The boundary also impedes further motion of the fluid. These effects at the boundary cause a swirling or other mixing of the fluid. The term "attenuation zone" refers to the area affected by the traveling wave. Activation of the transducer may be in a pulsed or constant fashion or any combination of constant and pulsed activation. In embodiments with multiple transducers, the transducers may be actuated together, separately, or in any sequence. Each individual transducer may also be individually activated in a constant or pulsed manner.

As indicated above, the fluid processing apparatus disclosed here can employ any of several different types of transducers and geometry. Any transducer can be used, such as a piezoelectric, magnetostrictive, thermoacoustic or electrostatic transducer, that efficiently converts electrical energy to acoustic energy at the proper frequency, which acoustic energy is, in turn, effective to cause adequate mixing of the fluid in the microfluidic junction of the manifold body. Examples of such transducers include Ferroperm PZT26. Piezoelectric thin film transducers for example, can employ any piezoelectric as the active material and any suitable substrate, provided the materials are sufficiently structurally robust and chemically inert for the intended use. The piezoelectric thickness generally will need to be between one-fourth and one half the wavelength at the selected frequency depending on acoustic matches at the fluid interface to operate on the most efficient fundamental thickness resonance. In accordance with certain preferred embodiments, transducers comprise a layer of pzt, such as Ferroperm PZT26, and, on two opposed sides, have an electrode. The electrode is usually silver or gold on a chromium adhesion layer. The radiation frequency (RF) is supplied with two conductors, one to each electrode.

Figure 1:
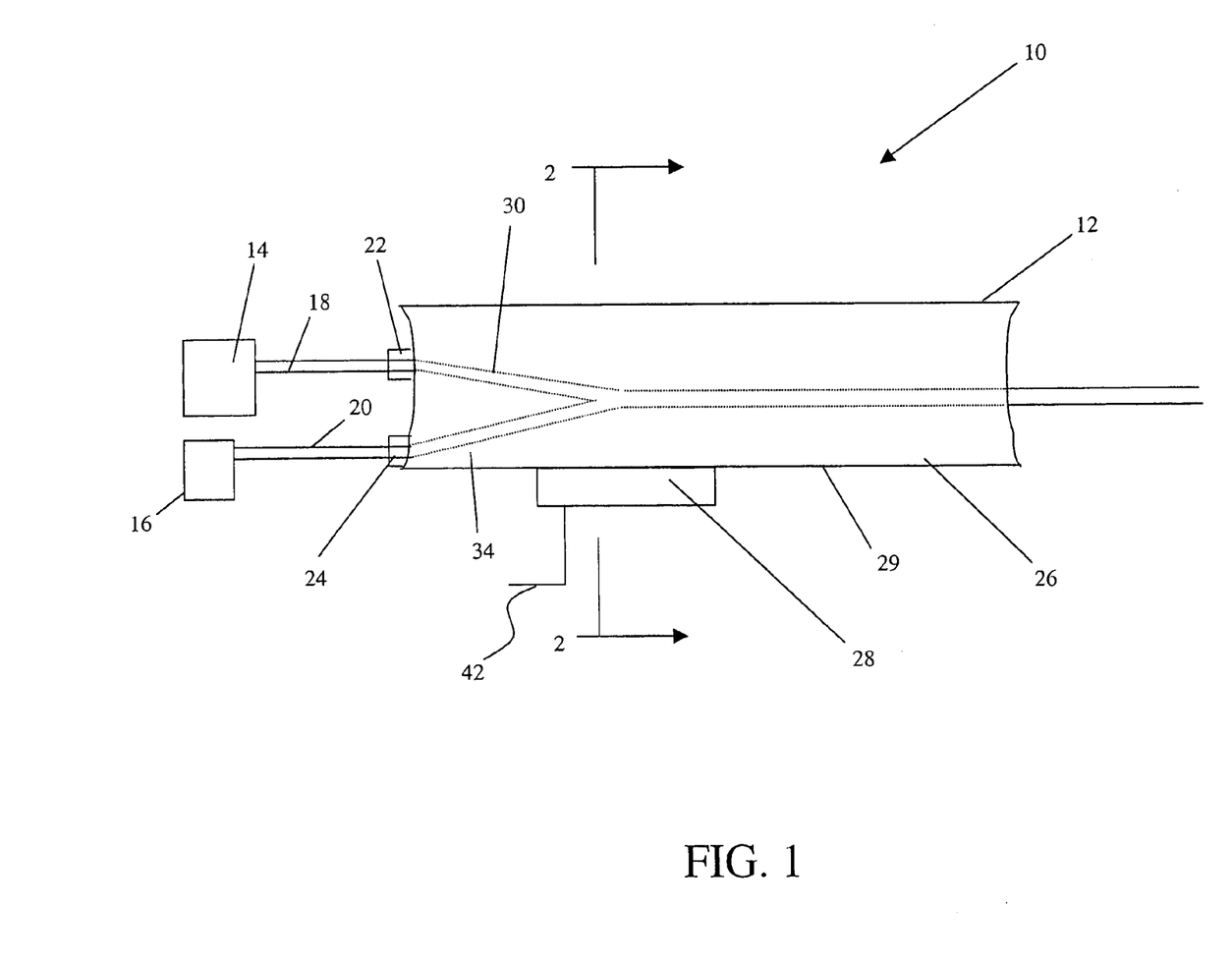
FIG. 1 is a schematic plan view of fluid processing apparatus in accordance with a preferred embodiment, comprising a fluid-handling manifold.
Figure 2:
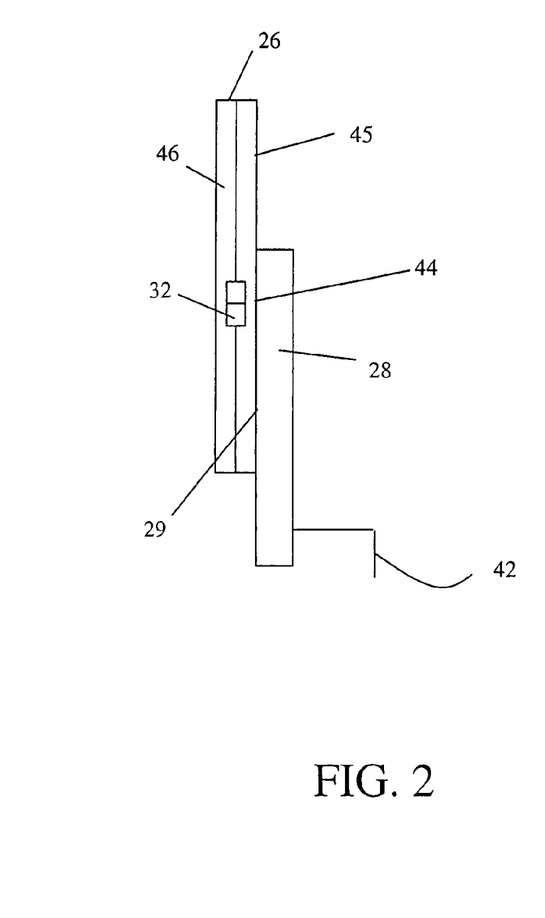
FIG. 2 is a cross-sectional view of the manifold body of the fluid-handling manifold of FIG. 1, taken along line 2-2 of FIG. 1.
Figure 3:
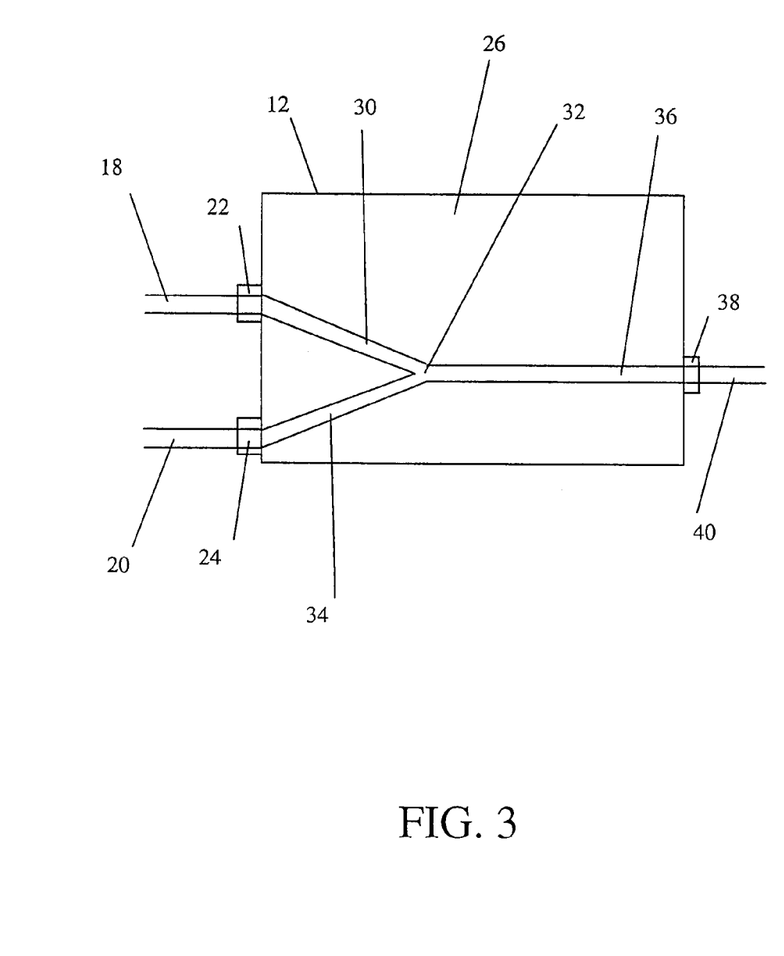
FIG. 3 is a cross-sectional plan view of the manifold body of FIGS. 1 and 2.

With reference to FIGS. 1-3, fluid processing apparatus 10 is seen to comprise fluid-handling manifold 12 as well as components 14 and 16 which are in fluid communication with fluid-handling manifold 12 via fluid lines 18, 20, respectively. Fluid line 18 is received by socket or nipple 22 of fluid-handling manifold 12 and fluid line 20 correspondingly is received by socket or nipple 24. Components 14 and 16 of the fluid processing apparatus may be, for example, a pump, reservoir, fluid sampling device or the like, or any combination of these devices. It should also be recognized that fluid processing apparatus 10 may in certain embodiments consist only of a self-contained fluid-handling manifold suitable for stand alone use and/or interconnection to other components.

Fluid-handling manifold 12 comprises a manifold body 26 and a transducer 28. Manifold body 26, in the embodiment shown in FIGS. 1-3, has a first fluid duct 30 extending internally within manifold body 26 from fluid connection 24 to a microfluidic junction 32. Similarly, manifold body 26 has a second fluid duct 34 extending within the manifold body to the microfluidic junction 32. As best seen in FIG. 3, microfluidic junction 32 is a faired connection of the first fluid duct 30 and second fluid duct 40 in the form of a Y-connection. Beyond microfluidic junction 32, an internal fluid duct 36 extends to fluidic connection nipple or socket 38 at which it makes fluid connection with fluid line 40. The microfluidic junction may be any number of shapes, sizes and configurations suitable for passing fluid. In certain embodiments the microfluidic junction may be substantially open. In other embodiments the microfluidic junction may be substantially closed. For example, such substantially closed fluid zones may include, but are not limited to capillary flow channels. Exemplary cross-sectional shapes include circular, rectangular, square and trapezoidal. It should be understood that in an alternative embodiment, outlet port 38 could serve as an inlet port and, likewise, either of fluid ducts 30 or 34 could serve as an outlet line. Ultrasonic acoustic traveling wave radiation generated by transducer 28 is used to process or treat fluid received by microfluidic junction 32. Thus, microfluidic junction 32 is operative to pass a linear or turbulent flow of fluid, optionally referred to in some instances here and in the claims below as a "local fluid flow" comprising fluid received from the first duct 30 and fluid received from the second duct 34.

It will be apparent to those skilled in the art, given the benefit of this disclosure, that one or more manifold bodies may be combined together in a fluid-handling manifold. One or more manifold bodies may be mounted on a suitable platform, encased in a suitable housing or otherwise packaged or mounted in a manner suitable for its intended use.

Transducer 28 is coupled to the microfluidic junction, such that it is coupled to any fluid present in the microfluidic junction. Transducer 28 is seen to overly surface 29 of manifold body 26. In certain preferred embodiments, if two laminar flow streams such as fluid flowing in fluid lines 18 and 20 are brought together, side by side, as it were, at say a Y-junction 32 they will stay relatively separated, according to the Reynolds number as they flow along the joined duct. If, for example, a traveling wave field force is generated by transducer 28 in it will push one fluid stream into the other fluid stream with the result of fast interstream mixing. It should be recognized that a manifold body of a fluid-handling manifold disclosed here may have any number of fluid ducts appropriate to the intended use of the device. Thus, while manifold body 26 in FIGS. 1-3 is shown with two inlet lines, each feeding a separate fluid duct, and a single outlet line, alternative embodiments may have more than two inlet ducts. A manifold body may form multiple microfluidic junctions. Optionally, some or all microfluidic junctions may be in communication with each other. Different inlet lines may be used to feed different fluids to a microfluidic junction at different times during a process. In addition, as discussed further below, manifold bodies are in accordance with alternative embodiments may have one or more additional components integral with the manifold body or otherwise incorporated into a fluid-handling manifold.

Transducer 28 is seen to be provided with a power signal input line 42. As discussed above, any suitable transducer may be used in the fluid-handling manifolds disclosed here, including piezoelectric transducers, magnetostrictive transducer, electrostatic transducer, thermo-acoustic transducer, and the like. It would be within the ability of those skilled in the art to select a suitable type of transducer, as well as a size and configuration for the transducer suitable for the intended use. It will also be within the ability of those skilled in the art, given the benefit of this disclosure, to select an operative frequency that is suitable for the intended use. Suitable frequencies typically fall within the range of about 6-200 MHz at 10-30 volts, physically about 20 volts, depending upon the size of the microfluidic junction. In accordance with other preferred embodiments, frequencies may typically fall within the range of 30-200 MHz. Microfluidic junctions of the present invention are not more than 300 microns across, measured from the active surface in the direction of traveling wave propagation. Above this size limit, it is found that power requirements become excessive and reduce commercial suitability.

As best seen in FIG. 2, manifold body 26 has an active surface 44 which contacts a local fluid flow within microfluidic junction 32. Active surface 44 in the embodiment of FIGS. 1-3 is not the surface of piezoelectric material or other active transducer material. Rather, it is seen to be the surface of lamination 45 of manifold body 26. Traveling waves generated by transducer 28 are propagated into the local fluid flow at surface 44 of laminate 45. For this purpose, transducer 28 is seen to overly surface 29 of manifold body 26. Also in this regard, it can be seen that microfluidic junction 32 is formed by matched recesses in the contacting surfaces of laminates 45, 46 of manifold body 26. In alternative embodiments wherein the manifold body is formed of more than two laminates, as disclosed above, a via may extend in a direction perpendicular or diagonal to the plane of the laminations so as to provide fluid communication body from a duct at one laminate interface or to another within one laminate plate. Such fluid communication can be provided either instead of or in addition to such via(s), by fluid lines on the surface or otherwise external to the manifold body. It will be recognized by those skilled in the art, given the benefit of this disclosure, that fluid-handling manifolds in accordance with the present disclosure are especially advantageous for the processing of liquids, such as aqueous liquids, hydrocarbon solvents, etc. In certain such applications, the non-reflective boundary toward which the active surface of the transducer of the fluid-handling manifold generates ultrasonic acoustic traveling radiation may be an air-liquid interphase.

Figure 4:
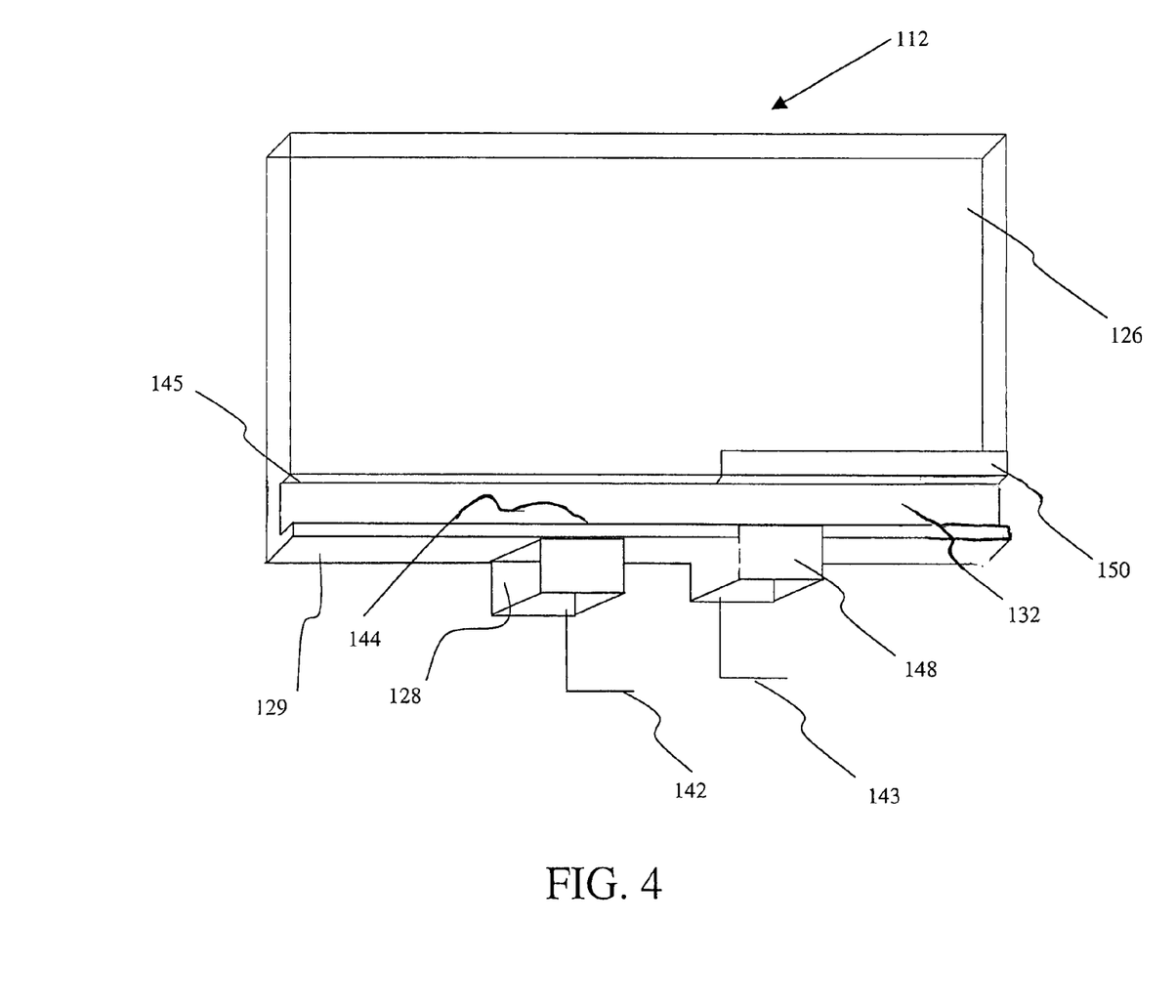
FIG. 4 is a cross-sectional perspective view, partially broken away, of a manifold body of a fluid-handling manifold of a fluid processing apparatus in accordance with an alternative embodiment.

Referring now to FIG. 4, an alternative embodiment is seen of a fluid-handling manifold Specifically, fluid-handling manifold 112 is seen in cross-sectional view, partially broken away. Manifold body 126 has an elongate microfluidic junction 132 with a square or otherwise or rectangular cross-sectional shape. Alternative suitable cross-sectional shapes include, for example, circular, oval, etc. The aspect ratio, that is, the height to width ratio may be smaller, such that an essentially planer flow channel is established. Fluid-handling manifold 112 of FIG. 4 further comprises a transducer 128 overlying surface 129 of manifold body 126. Transducer 128 has power signal input line 142 and is operative to generate ultrasonic acoustic traveling wave radiation into fluid in microfluidic junction 132 from active surface 144. The surface or wall 145 of microfluidic junction 132, opposite of active surface 144, is a non-reflective boundary of the microfluidic junction. That is, it is a fluid boundary for the local fluid flow through the microfluidic junction, but it is substantially non-reflective of traveling wave radiation generated from active surface 144. Non-reflective boundary 145 is not more than 300 microns from the active 144.

Fluid-handling manifold 112 further comprises a second transducer 148 partially embedded into the manifold body 126, such that active surface 149 of second transducer 148 contacts the local fluid flow through microfluidic junction 132. Opposite active surface 149 is a reflective boundary 150. In the embodiment shown in FIG. 4, reflective boundary 150 comprises an embedded material that is substantially reflective of ultrasonic acoustic radiation generated at the active surface 149 of transducer 148. Accordingly, a standing wave can be established in the portion of microfluidic junction 132 between transducer 148 and the reflective boundary 150. Transducer 148 has an input power signal line 143 and can be actuated either simultaneously with transducer 128, sequentially, alternatingly, or in accordance with other timing suitable to the intended purpose of the fluid-handling manifold. The manifold bodies of the fluid-handling manifold disclosed here, in accordance with preferred embodiments, are operative at fluid pressures of at least 25 psi. That is, they are fluid tight and operable at 25 psi. Certain especially preferred embodiments are operable at much higher pressures required for fluid processing such as, for example, liquid chromatography, e.g. HPLC. Such embodiments are operative at fluid pressure in the microfluidic junction of at least 1000 psi, more preferably at least 6000 psi. Certain embodiments are operative at fluid pressure in the microfluidic junction exceeding 10,000 psi. In this regard, it should be recognized that the fluid-handling manifold disclosed here may at times have fluid, for example an aqueous fluid, sitting static in some or all of its fluid ducts. At other times fluid will be flowing in some or all of its fluid ducts. At other times there may be no fluid being processed in the fluid ducts, such that the ducts typically would have purge gas or atmospheric air within them.

It can be seen that the first and second transducers in the embodiment of FIG. 4 are axially spaced from each other in the direction of flow through the microfluidic junction and are radially aligned with other along the microfluidic junction. That is, the radiation propagated from each is axially spaced but substantially in the same direction orthogonal to the local fluid flow through the microfluidic junction. In an alternative embodiment similar to FIG. 4, both the first and second transducers, and optionally one more additional transducer, may each be operative to generate ultrasonic acoustic traveling wave radiation into the microfluidic junction substantially orthogonal to local fluid flow from an active surface toward a non-reflective boundary not more than 300 microns from the active surface. Such spaced transducers may be actuated in accordance with any timing pattern suitable to the intended use, e.g., simultaneously, sequentially, alternatingly or otherwise. In yet other similar embodiments, a line of transducers may alternate from one side of the microfluidic junction to the other. Such interdigitized transducers may be actuated in accordance with any timing pattern suitable to the intended use. Additional embodiments employing alternative positioning of multiple transducers at a microfluidic junction will be apparent to those skilled in the art given the benefit of this disclosure.

Figure 5:
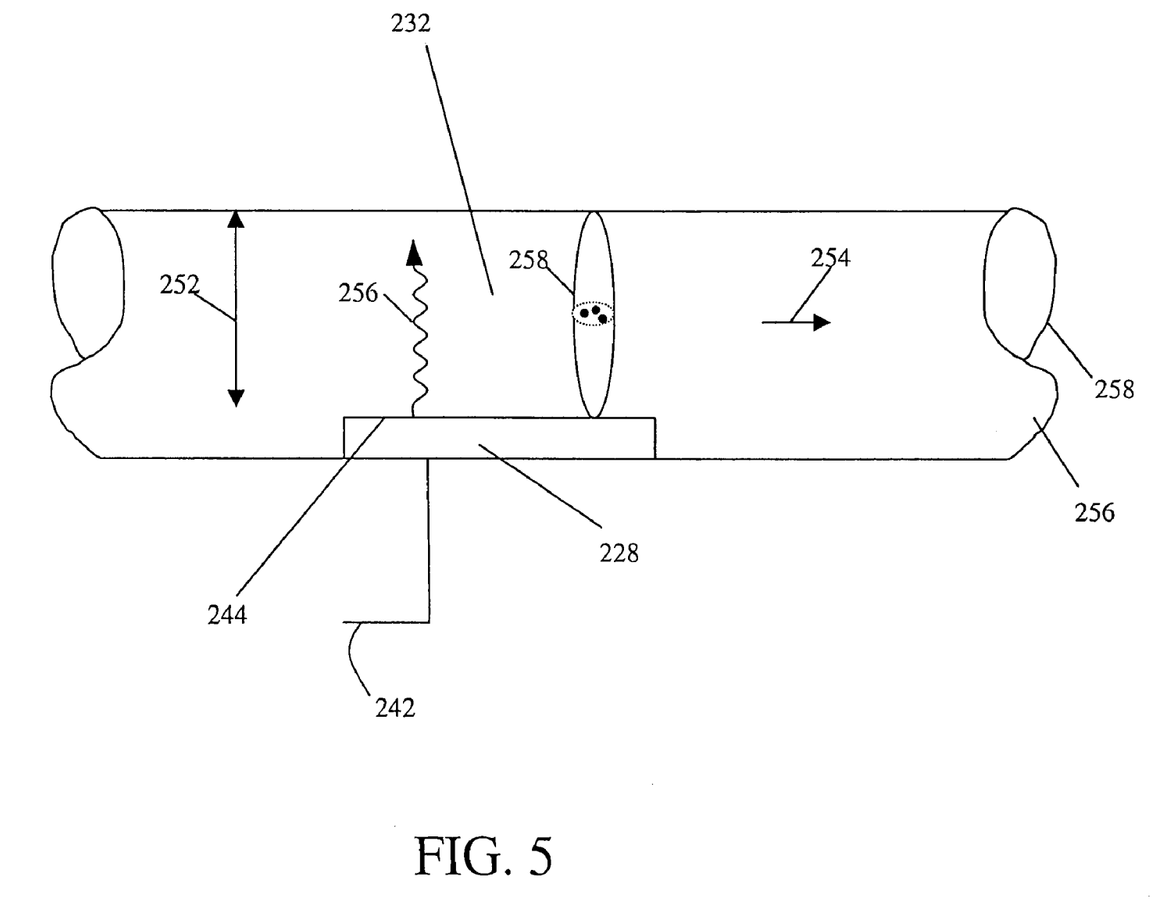
FIG. 5 is a schematic view, partially broken away, of a fluid duct and associated transducer of a manifold body of fluid-handling manifold of a fluid processing apparatus in accordance with an alternative embodiment.

Referring now to FIG. 5, a schematic view is seen of a microfluidic junction of a manifold body in accordance with the present disclosure. Specifically, elongate microfluidic junction 232, having a circular cross-sectional shape, extends over active surface 244 of transducer 228. Electrical signal line 242 is operative to feed an actuation signal to the transducer 228. The distance from active surface 244 to the farthest opposite point, represented by line 252 in FIG. 5 is not more than 300 microns. Microfluidic junction 232 carries a local flow of fluid, such as an aqueous liquid fluid, represented by arrow 254. Transducer 228 is actuated in FIG. 5 to generate ultrasonic acoustic traveling wave radiation 256 and ultrasonic acoustic standing wave 258, each in a direction substantially orthogonal to local fluid flow 254. The traveling wave and standing wave radiation may be actuated in any timing pattern suitable to the intended use. In certain embodiments it may be beneficial to generate a standing wave first to trap particles in the fluid, and then to generate a traveling wave for mixing in the vicinity of the particles. In certain embodiments the mixing effect caused by traveling wave radiation may mix two or more liquids to create (e.g., to precipitate) particulate matter. A standing wave can then be generated to capture or move the particulate matter. According to certain preferred embodiments, if the same transducer produces a standing wave and traveling wave simultaneously then it may be preferable to provide part of the propagated wave with two separate geometrically displaced boundaries; one reflecting and one not. In another preferred embodiment, the same transducer, with very rapid tuning to and away from a resonant cavity setting, could be used to produce a standing wave and a traveling wave simultaneously. An example of using the same transducer to produce a standing wave and a traveling wave simultaneously is to produce one standing wave field with a <300 micron pathlength to trap particles, such as silica C18 beads, and another separate standing wave field, at right angles to the first, to propel, by quartz wind effect, a colored dye through the trapped beads.

Figure 6:
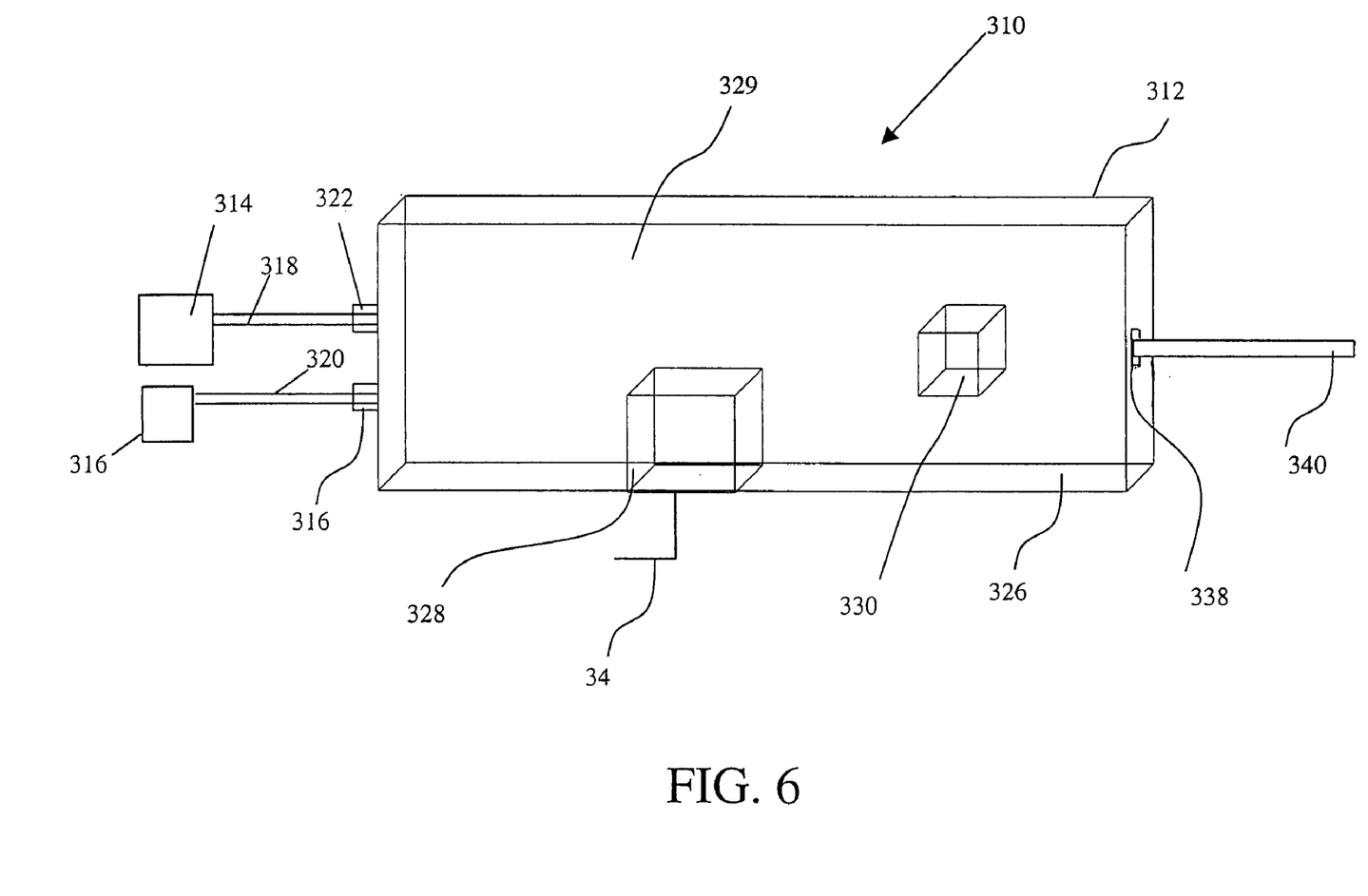
FIG. 6 is a schematic perspective view of a fluid processing apparatus in accordance with an alternative embodiment.

Referring now to FIG. 6 an alternative embodiment is illustrated of a fluid processing apparatus in accordance with this disclosure. Specifically, fluid processing apparatus 310 is seen to comprise components 314 and 316 each of which is operative to feed fluid to manifold body 326 of fluid-handling manifold 312 via feed lines 318, 320, respectively, to inlet ports 322, 324, respectively. Fluid-handling manifold 312, in addition to manifold body 326, further comprises a transducer 328 having signal feed line 342 and additional fluidic component 330. Transducer 328 is seen to overly surface 329 of the manifold body. Additional fluidic component 330 also is integral with the manifold body at surface 329. An outlet line 340 from outlet port 338 is operative to carry fluid treated in a microfluidic junction of the manifold body by transducer 328. Operative component 330 is operative on fluid in the manifold body, optionally being operative directly on a local fluid flow within the microfluidic junction. Alternatively, fluidic component 330 is operative on fluid in a duct remote from the microfluidic junction. In accordance with certain preferred embodiments, the fluidic component 330 is a mechanical mixer operative to mix fluid in the manifold body, e.g., to mix fluid in the microfluidic junction or in a fluid zone remote from the microfluidic junction, for example, in a fluid holding reservoir, duct etc. In accordance with alternative embodiments, microfluidic component 330 is a sensor operative to detect a condition of fluid in the manifold body. In accordance with certain such embodiments, the sensor is operative to detect the temperature of fluid in the manifold body. In accordance with alternative embodiments the sensor is operative to detect the pressure of fluid in the manifold body. In accordance with yet other such embodiments the sensor is operative to detect an optical property of fluid in the manifold body, for example, turbidity, transmittance, reflectance, light absorption (e.g., the absorbance of specific wave lengths), color, transparency etc. In accordance with yet other such embodiments, the sensor is operative to detect fluid flow rate of fluid in the manifold body. The sensor may, for example, be a Hall effect sensor.

In accordance with yet other embodiments the sensor may be a dielectric constant sensor. In accordance with yet other embodiments the sensor may be a viscosity sensor. In accordance with other embodiments, component 330 may be a window providing visual observation of fluid in the manifold body. Such window may be formed, for example, of a visually transparent plate or pane forming some or all an external lamination of a laminated manifold body. In accordance with yet other embodiments the sensor may be a pH meter. Fluidic component 330 may, for example, be operative to heat fluid in the manifold body or to cool such fluid. In accordance with alternative embodiments of this type, the fluidic component 330 may be a valve operative to control a flow of fluid in the manifold body. For example, in accordance with certain such embodiments, the transducer may be operative to generate ultrasonic acoustic traveling wave radiation into fluid in the valve. In accordance with alternative embodiments, fluid component 330 may comprise a fluid pump operative to pump the fluid through the microfluidic junction or to other locations inside the manifold body or out of the manifold body. In accordance with alternative embodiments, fluid component 330 is operative to control a temperature of fluid in the manifold body. Here, as in other embodiments, the fluidic component 330 may be operative to treat all fluid resident in the manifold body or all fluid entering or leaving the manifold body, may be operative to treat only the portion of the fluid or only certain components of the fluid in the manifold body.

Embodiments of the present invention have been described above by way of examples only, and it will be apparent to a person skilled in the art that modifications and variations can be made to the described embodiments without departing from the scope of the invention as defined by the appended claims. If any of the meanings of the terms or phrases in the present application are in conflict with the meanings of the terms or phrases in the applications, patents and/or publications incorporated herein by reference, the meanings of the terms and phrases of the present application are intended to be controlling.

What is claimed is:

1. Fluid processing apparatus comprising a fluid-handling manifold comprising:
  a manifold body having fluid ducts comprising at least a first fluid duct, a second fluid duct, a microfluidic junction, and an internal fluid duct, the first fluid duct and the second fluid duct being in fluid communication with each other at the microfluidic junction, the microfluidic junction being operative to pass into the internal fluid duct a local fluid flow comprising fluid received from the first fluid duct and fluid received from the second fluid duct;
  a transducer operative to generate ultrasonic acoustic traveling wave radiation of at least one wavelength into local fluid flow from a first surface area of the fluid ducts toward a second surface area of the fluid ducts, wherein the second surface area is directly opposite and not more than 300 microns from the first surface area;
  wherein the second surface area is non-reflective of said wavelength; and
  a sensor integral with the fluid-handling manifold and operative to detect a condition of fluid in the manifold body.

2. Fluid processing apparatus comprising a fluid-handling manifold comprising:
  a manifold body having fluid ducts comprising at least a first fluid duct, a second fluid duct, a microfluidic junction, and an internal fluid duct, the first fluid duct and the second fluid duct being in fluid communication with each other at the microfluidic junction, the microfluidic junction being operative to pass into the internal fluid duct a local fluid flow comprising fluid received from the first fluid duct and fluid received from the second fluid duct; and
  a transducer operative to generate ultrasonic acoustic traveling wave radiation of at least one wavelength into local fluid flow from a first surface area of the fluid ducts toward a second surface area of the fluid ducts, wherein the second surface area is directly opposite and not more than 300 microns from the first surface area;
  wherein the second surface area is non-reflective of said wavelength.

3. The fluid processing apparatus in accordance with claim 2 wherein the transducer is operative to generate ultrasonic acoustic traveling wave radiation into the microfluidic junction substantially orthogonal to a local fluid flow through the microfluidic junction.

4. The fluid processing apparatus in accordance with claim 2 further comprising a fluidic component integral with the fluid-handling manifold and operative on fluid in the manifold body.

5. The fluid processing apparatus in accordance with claim 4 wherein the fluid component is a sensor operative to detect a condition of fluid in the manifold body.

6. The fluid processing apparatus in accordance with claim 5 wherein the sensor is operative to detect an optical property of fluid in the manifold body.

7. The fluid processing apparatus in accordance with claim 4, further comprising a second fluidic component integral with the fluid-handling manifold and operative on fluid in the manifold body, wherein the fluidic component comprises an optical sensor operative to detect a condition of fluid in the manifold body, and wherein the second fluidic component comprises a valve operative to control a flow of fluid in the manifold body.

8. The fluid processing apparatus in accordance with claim 7, wherein the sensor is operative to detect the temperature of fluid in the manifold body.

9. The fluid processing apparatus in accordance with claim 7, wherein the sensor is operative to detect an optical property of fluid in the manifold body.

10. The fluid processing apparatus in accordance with claim 7, wherein the valve is operative to control the flow of fluid out of the manifold body.

* * * * *